(12) United States Patent
Bepperling et al.

(10) Patent No.: US 6,416,736 B1
(45) Date of Patent: Jul. 9, 2002

(54) USE OF HEMOGLOBIN DERIVATIVES FOR DETERMINING PLASMA AND/OR BLOOD VOLUME

(75) Inventors: Frank Bepperling, Bad Nauheim; Wolfram Eichner, Butzbach; Klaus Sommermeyer, Rosbach v.d.H.; Jens Opitz, Frankfurt, all of (DE)

(73) Assignees: Fresenius Kabi Deutschland GmbH; R&D Center, both of Friedberg (DE)

( * ) Notice: Subject to any disclaimer, the term of this patent is extended or adjusted under 35 U.S.C. 154(b) by 0 days.

(21) Appl. No.: 09/613,815

(22) Filed: Jul. 11, 2000

(30) Foreign Application Priority Data

Jul. 14, 1999 (DE) .......................................... 199 33 275

(51) Int. Cl.⁷ .............................................. A61K 49/00
(52) U.S. Cl. ...................................................... 424/9.1
(58) Field of Search ........................................... 424/9.1

(56) References Cited

U.S. PATENT DOCUMENTS 3,964,865 A * 6/1976 Das ............................. 23/230

* cited by examiner

*Primary Examiner*—Dameron L. Jones
(74) *Attorney, Agent, or Firm*—Nixon & Vanderhye P.C.

(57) ABSTRACT

The invention concerns the use of hemoglobin derivatives for determining plasma and/or blood volume, wherein the hemoglobin derivatives are stable chromoproteins with a molecular weight of at least 64 kDa. The use can encompass the treatment of a patient wherein (a) a defined quantity of hemoglobin derivative is applied to a patient, (b) the mixing of hemoglobin derivative with the blood of the patient is awaited, (b) at least one sample is taken from the patient, (c) the content of the hemoglobin derivative and/or the content of the hemoglobin derivative bound ligand in the sample is determined and (d) the plasma and/or blood volume ascertained therefrom.

The invention also concerns preparations for determining plasma and/or blood volume which contain hemoglobin derivatives and are characterized in that the hemoglobin derivatives are stable chromoproteins with a molecular weight of at least 64 kDa which carry at least in part carbon monoxide as ligand, as well as processes for their manufacture.

24 Claims, No Drawings

USE OF HEMOGLOBIN DERIVATIVES FOR DETERMINING PLASMA AND/OR BLOOD VOLUME

The present invention relates to the use of hemoglobin derivatives for determining plasma and/or blood volume as well as preparations for determining plasma and/or blood volume, which contain a hemoglobin derivative with carbon monoxide as ligand.

We describe as blood volume the entire quantity of blood circulating, which is composed of plasma volume and erythrocyte volume. An adequate blood flow through the organs is necessary for the maintenance of all organ functions. Losses of blood and fluid lead to an uneven distribution of blood volume for the maintenance of vital functions. In such cases, it may come about that there is a reduced blood flow through some organs and damage to these as a consequence. The volume of plasma as a measure for the state of the filling of the cardio-vascular system and for determining an adequate blood flow in patients with blood or fluid loss is thus of great significance for clinical daily practice and for research.

In the prior art therefore a number of processes have been developed with which plasma and/or blood volume can be determined.

Standard processes for determining the volume of erythrocytes and of plasma volume by the use of radio-active labelling had already been proposed in 1973 by the International Society for Hematology (British Journal of Hematology, Vol. 25 (1973), 801–814). For determining volume of erythrocytes, a process was recommended wherein the erythrocytes of a patient are mixed with a solution that contains $^{51}Cr$, the mixture is incubated for 15 minutes and finally the erythrocytes are obtained and washed. The radioactive labelled erythrocytes are injected again into the patient. 10 and 20 minutes after the injection, blood samples of 5 to 10 ml are taken from the patient, in which the erythrocytes are lysed and the volume can be determined by means of the radioactivity measured.

In the corresponding process for determining plasma volume, human serum albumin labelled with radioactive iodine is given to the patient's plasma. The taking of samples and assessment ensues in essence as with the process for determining erythrocyte volume.

In view of the radiation loading, routine injection, especially repeated input of radioactively marked isotopes, is completely excluded in clinical daily practice. Correspondingly, these standard procedures are only used for scientific purposes or with special disease patterns, as for example polycythemia true.

Furthermore, in the prior art processes were developed for determining plasma volume, where dye compounds were introduced into the blood of patients as analytes. Here, for example, Evans Blue or Indocyanin green (ICG) are injected intravenously and the concentration of dye is determined spectrometrically or densitometrically after mixing with the blood plasma and taking of a sample (Haller et al, Anaesthetist, Vol. 41 (1992), 115–120; and Gehring et al., Infusion therapy and Transfusion medicine, Vol. 23 (1996), 86–91). It is possible to ascertain the plasma volume from the dilution of the dye by the plasma. However, it has emerged that these processes involve some risks to the patients. The dye Evans Blue is under suspicion of possessing mutagenic properties and thus is unsuitable for determining plasma volume in humans. The introduction of ICG should ensue centre-venously or centre-arterially and the samples should be taken arterially. It is therefore necessary to apply centre-venous and/or arterial catheters in order to perform the measurement. The application or insertion of the catheters is not without dangers to the patients and very costly. What is more, ICG which is bound with the plasma protein, interferes with pulsoximetry, a clinically routinely applied non-invasive process for the determining of oxygen saturation (Scheller et al., Anesthesiology, Vol. 65 (1986), 550–552) and merely possesses a plasma half value time of 3.2 min. The dye is eliminated exclusively by the liver (Haller et al, in the stated place). With plasma protein losses, for example, extravasation of albumin following burns, too high plasma volumes are found when determining plasma volume because of the binding of ICG to plasma proteins.

Although determining the plasma volume with ICG has already been known in the prior art for over 30 years (Bradley, E. C. and Barr J. W., Life Sci., Vol. 7 (1968), 1001–1007), it was not possible to implement this process in clinical daily practice, because of the problems mentioned.

The determining of the volume of erythrocytes by labelling with the dye fluorescein has already been carried out in the prior art (Ohrt et al., Ansth. Analog., Vol. 87 (1998), 1234–1238). This is used to label the erythrocytes of a patient with fluorescein and re-inject these into the patient. After mixing with the blood, samples are taken and an analysis is made for the content of fluorescein by flow cytometry. Because of the fact that the marking of erythrocytes and the subsequent analyses lasts more than an hour, the applicability of this process is limited to those problem areas where an acute determination of the volume situation is of low relevance.

Finally, there have been developed processes for determining blood volume in which a defined quantity of carbon monoxide is given to the patient into breath-ventilation and finally the carbon monoxide saturation of the blood is determined (Christensen et al., Anaesthesiol. Scand., Vol. 730, (1993), 622–627; and Poulsen et al., Eur. J. Appl. Physiol., Vol. 77 (1998), 457–461). The application of a defined carbon monoxide quantity is very costly and limited to patients who are ventilated artificially.

According to a further embodiment of this process, blood is taken from patients and treated with carbon monoxide. The erythrocytes which contain hemoglobin bound with carbon monoxide, are reinjected and the concentration of carbon monoxide in the blood is determined after thorough mixing and sample taking (Obata et al., British Journal of Anaesthesia, Vol. 81 (1998), 940–944). This process reduces however the capacity of the blood to transport oxygen, as a part of the blood of the patients is prevented from absorbing the oxygen because of the bound carbon monoxide. These processes can therefore not be applied to patients with low oxygen reserves.

In view of the problems described in the prior art regarding processes for immediate determining of plasma and/or blood volume these are not routinely applied in clinical daily practice. The condition of the volume of the patients today is thus ascertained as before indirectly through measuring the hemodynamic circulation parameters such as blood pressure, heart pulse, pulmonary pressures and heart pace volumes. These measurements, however, do not allow any statement about the total and peripheral blood and plasma volumes.

It is therefore the problem underlying the present invention to make available a method which can be used for determining the blood and plasma volume in clinical daily practice.

This problem is solved in accordance with the invention by use of hemoglobin derivatives for determining plasma and blood volume. The hemoglobin derivatives are stable chromoproteins with a molecular weight of at least 64 kDa.

In the context of the present invention, it could be shown surprisingly, that these hemoglobin derivatives are particularly suited for determining plasma volume, as the hemoglobin derivatives and/or ligands bound with these are meaureable in low concentrations. This means that application of hemoglobin is possible in a quantity which does not bring about an alteration in the volume or a change in other parameters of the blood.

Further, the present invention concerns the use of hemoglobin derivatives in a diagnostic process for determining plasma and/or blood volume, wherein a defined quantity of corresponding hemoglobin derivative is given to a patient and the mixture of hemoglobin derivatives with the patient's blood is awaited, at least one sample is taken from the patient, the content in hemoglobin derivative or the content in hemoglobin-derivative bound ligands in the sample is determined, and the plasma and/or blood volume ascertained.

The dilution of the applied hemoglobin derivative can thus either ensue through determining the hemoglobin concentration in the blood or plasma and/or through determining the concentration of the hemoglobin derivative bound ligands.

Further embodiments of the present invention are preparations for determining plasma and/or blood volume that contain derivatives and to which at least in part carbon monoxide is bound as a ligand. In a preferred embodiment, the hemoglobin derivatives are completely saturated with carbon monoxide.

In the context of the present invention, there is thus made available by the use of hemoglobin derivatives the possibility for the first time of determining the plasma and/or blood volume by means of a simple, rapid and safe procedure, which fulfils all the conditions for application in daily clinical practice.

Hemoglobin is a chromoprotein with a molecular weight of 64 Kilodalton (kDa). The protein consists of two $\alpha$- and $\beta$-globin chains, which respectively have bound a heme as a prosthetic group. Isolated hemoglobin molecules are unstable and disintegrate rapidly into the more stable $\alpha$- and $\beta$-dimers with a molecular weight of 32 kDa.

In the context of the present invention, molecules are designated as "hemoglobin-derivatives" which contain $\alpha$- and/or $\beta$-globin chains which are linked intra-molecularly, in order to obtain a stable chromoprotein with a molecular weight of at least 64 kDa. Preferably, the hemoglobin derivatives consist of two $\alpha$- and two $\beta$-globin chains.

The coupling can for example ensue through covalent binding of the globin chains as well as through the fusion of the genes which code for globin chains. Such coupling products consisting of $\alpha$-/$\alpha$-hemoglobin chains which are tied by means of a "coupling agent" were already described in the prior art (EP 402 300, EP 700 997 U.S. Pat. No. 5,884,090 or Kerwin et al., J. of Pharmaceutical Science, Vol. 88:1, (1999) 79).

It goes without saying that the term hemoglobin derivatives encompasses also hemoglobin molecules whose primary structure was changed through substitutions, deletion or addition of amino acid, insofar as the invention-essential properties of the derivatives (chromoprotein with a molecular weight of al least 64 kDa) are not essentially impaired by these changes. Corresponding allelic variants of hemoglobin naturally emerge or can be produced through recombination. Kerwin et al. (in the stated place) use for example a known mutation of the hemoglobin in order to produce a hemoglobin derivative with reduced oxygen affinity. WO 98/50430 describes changes in the primary structure of hemoglobin which effect an improved solubility or a reduced nitrogen binding of the molecule.

The term hemoglobin derivatives encompasses furthermore hemoglobin molecules which were inter-molecularly coupled for the creation of hemoglobin polymer forms or coupled to ligands, such as for example polyethylene glycol (PEG; cf. U.S. Pat No. 5,478,806) or hydroxy ethyl starch (HES; cf. WO 98/01158) and/or to other polymers. The intermolecular linking can occur before, simultaneously with or after the intramolecular coupling. On binding to a ligand the intramolecular linking ensues by reaction with which the globin chains are bound with the ligand.

The hemoglobin which can be used for the production of derivatives can be of human, animal, or recombinant origin. In the literature, various processes were described for the production of recombinant hemoglobin (expression in bacterial, yeast, or animal cells, as well as in transgene plants or animals).

The production of such hemoglobin derivatives for obtaining "hemoglobin based oxygen carriers" (HBOCs) is described comprehensively in the prior art (Benesch, Meth. Enzymol., Vol. 231 (1994), 267–274; Keipert et al, Transfusion, Vol. 29 (1989), 767–773; Snyder et al., Proc-.Natl. Acad. Sci. USA, Vol. 84 (1987), 7280–7284; Rogers et al., Biochim. et Biophys. Acta, Vol. 1248 (1995), 135–142; Hai et al., Art. Cells, Blood Subs. And Immob. Biotech., Vol. 22(3) (1994), 923–931; DE 26 07 706, DE 26 16 086; EP 646 130; EP 290 252; EP 277 289; WO 98/0115; U.S. Pat. Nos. 4,911,929; 4,861,867; 4,857,636; 4,777,244; 4,698,387; 4,600,531; 4,526,715; 4,473,494; and 4,301, 144). For the present invention, any hemoglobin derivative can be used whereby it is not required in the context of the present invention that these derivatives able to bind oxygen reversibly.

The intra-molecularly linked hemoglobin has a molecular weight of at least 64 kDa, whereas coupled hemoglobin derivatives or conjugates with a molecular weight of at least 128 kDa are particularly preferred. Molecules of this size have the advantage in particular that they are able to leave intra-vasal space only to a very slight extent. The determination of too high a plasma and/or blood volume because of an extravasation of the analytes is thereby excluded. Preferably, the hemoglobin derivatives should not exceed an upper limit of 700 kDa for use according to the present invention, where molecular weight of up to 500 kDa is particularly preferred.

The process for production of the inventive preparation for determining plasma and blood volume can encompass a mixture of the hemoglobin derivative with a physiological solution, or if needs be with a suitable auxiliary or carrier substance. Here, any carrier and/or auxiliary substance known in the prior art can be used (e.g. Ringer's lactate, sodium chloride, sodium phosphate, polysorbate and/or solutions containing EDTA; for a general overview, cf. Kerwin et al., at the stated place).

There are a number of conditions (e.g. temperature and time) described in the prior art whereby hemoglobin derivatives can be stored independently of the ligand in a stable way. These conditions can come into play in the context of the present invention. In order to prevent oxidation of the hemoglobin into methemoglobin during storage, for example a reducing agent or a stabilizer can be added. The use of ascorbic acid, N-acetyl tryptophane or N-acetyl cystein is preferred as stabilizer.

The packaging of hemoglobin derivatives can ensue in any container described in the prior art. According to one embodiment of the invention, glass or plastic containers are used for packaging, wherein the use of oxygen-impermeable containers for hemoglobin derivatives are preferred. According to one particularly favoured embodiment of the invention, hemoglobin derivatives in their oxy-or desoxy-form, and so without ligands or with oxygen as ligands, are stored in oxygen-impermeable containers.

Further, wrappings made out of ethyl-vinyl acetate (EVA), polyethylene (PE), polyamide (PA), polyolefines, polyvinylchloride (PVC) or combination wrappings, e.g. made up out of PE/PA, can be used. Another possibility of packaging consists of introducing hemoglobin derivatives into ready to use syringes.

Processes for the further reduction of the oxygen-content during or after packaging are also known in the prior art, (cf. Kerwin et al, 1999, in the stated place) and can be used in the context of the present invention. Oxygen-permeable packaging materials can additionally be packed in an oxygen-impermeable sleeve which can otionally contain oxygen absorbers, e.g. Ageless.

The inventive use of hemoglobin derivatives for determining plasma and/or blood volume can include steps whereby a defined quantity of the hemoglobin derivative is applied to a patient, the mixing of the hemoglobin derivative with blood is awaited, at least one sample is taken from the patient, the content of the hemoglobin derivative or the content of the hemoglobin derivative bound ligands in the sample determined and the plasma and/or blood volume is ascertained.

According to another aspect, the inventive use of hemoglobin derivatives for determining plasma and/or blood volume makes it possible to give a hemoglobin derivative to patients with blood loss which works at the same time as an oxygen carrier and can be used for determining plasma and/or blood volume.

The inventive use of hemoglobin derivatives in diagnostic processes for determining blood and plasma volume can be carried out both in humans and animals.

According to one preferred embodiment of the invention, the application of hemoglobin derivatives ensues by injection through central or peripheral veins. In principle, the quantity of the hemoglobin derivative to be applied should be kept as low as possible, so that the minimum level is determined by the detection level of the derivative in the following analysis. The detection level itself depends in particular cases again on the analysis process used.

The quantity of hemoglobin derivatives to be applied respectively can easily be determined by the person skilled in the art independently of the named parameters in particular cases. Preferably, 0.05 to 0.3 g/kg of body weight of hemoglobin derivative is applied.

After application of the hemoglobin derivative this is completely mixed with the blood of the patient within a few minutes. The speed of distribution depends here on the manner of application and of the clinical situation of the patient.

Finally, at least one sample of blood is taken from the patient whereas the taking of two to three samples is preferred. The samples can for example be taken intra-arterially or intravenously. The volume of the sample is selected in such a way that an analysis of the concentration of hemoglobin derivative and/or of the bound ligands of this derivative in the sample is possible. According to a preferred embodiment of the invention at most 2 to 3 ml of blood are taken.

Determining hemoglobin concentration in the sample can ensue as per processes known in the prior art. For example, the Drabkins process can be used (International committee for Standardization in Hematology in J. Clin. Path., Vol. 18 (1965), 71–75; and Br. J. Hematology., Vol. 13 (1997), 71–75). As an alternative to this, the concentration of hemoglobin can be determined by means of the aca® DuPont Discrete clinical analyzer, which implements the determination according to a variant of the Drabkins process (cf. instructions of the manufacturer, "Method 91"). Both processes use an optical measurement principle. Finally, the hemoglobin concentration can be determined also by means of a hemolytic index on a Hitachi analysis device.

The concentration of the analyte can be measured on a standard curve from the measured absorption or extinction of the hemoglobin derivative. The standard curve can be drawn up, for example, by determination of the absorption or extinction of at least two known concentrations of the hemoglobin derivative. The preparation of a standard curve using at least four concentrations of hemoglobin derivative is however preferred.

It can be of advantage in determining plasma and/or blood volume to take a sample from the patient before the input of hemoglobin derivative, so as to determine the concentration in plasma hemoglobin before injection of the derivative (determination of the "nil value").

According to a particularly preferred embodiment of the invention, several samples are taken from the patient after injection of the hemoglobin derivative for determining plasma and/or blood volume, so as to determine the plasma-hemoglobin concentration at the actual time of the injection (actual time $t_o$) and thus the concentration of the hemoglobin derivative, which theoretically would be present at the application and simultaneous complete mixing. To this end, for example, the person to be examined could have two to three blood samples taken, in order to ascertain via extrapolation of the regression line the concentration at the actual time $t_o$.

The plasma volume of the patient can be calculated from these values. According to a preferred embodiment of the invention the plasma volume is calculated according to the formula $$PV = D/C_{OPlasma}$$

wherein

PV is the Plasma volume (in ml)

D is the administered dose of hemoglobin derivative (in mg) and $C_{OPlasma}$ is the concentration of hemoglobin in the plasma at the actual time of injection, wherein $C_{OPlasma}$ is obtained from the plasma hemoglobin concentration of the derivative determined by means of the regression line minus the concentration of plasma hemoglobin before injection of the derivative ("nil-value").

According to another embodiment of the invention the blood volume can be calculated from the plasma volume by the following formula:

$$BV = PV \cdot 100/(100 - \text{Hematokrit}),$$

wherein BV is the blood volume.

According to an alternative embodiment of the invention the plasma and blood volume is determined via the concentration of the hemoglobin derivative bound ligand.

Self-evidently, the measurement of the concentration of the hemoglobin derivative and of the concentration of the ligand bound thereby can be performed using one sample wherein the analysis processes differ from one another.

On determining the concentration of the hemoglobin bound ligand it is particularly preferred according to the invention to use hemoglobin derivatives which at least in part have carbon monoxide as a bound ligand.

The carbon monoxide content in blood in humans amounts normally to 0 up to 0.8 Vol. % in relation to the carbon monoxide content in breathed air (Manual of clinical chemistry and pathobiochemistry, $3^{rd}$ edn., tab. 6.4-6), whereas in exceptional cases up to 2.3% has been measured. In the case of smokers, the value amounts to up to 5%. The input of carbon monoxide bound to hemoglobin derivatives is thus without danger for the patient, since carbon monoxide naturally occurs in blood and does not impair the oxygen carrying capacity of the patient's own blood.

Determining plasma and/or blood volume can ensue with this embodiment via determining of carbon monoxide content of the blood. This procedure has the particular advantage that determining of carbon monoxide content in normal blood can be carried out with particularly small sample quantities and in a very short time. A further advantage of this procedure is the high accuracy of the measurement.

In this embodiment of the invention it can also be advantageous to take at least one sample from the patient before the input of the carbon monoxide bound to hemoglobin derivatives, so as to determine the concentration of the carbon monoxide in the blood of the patient before the input of additional carbon monoxide (ascertaining the "nil-value").

The application of the hemoglobin derivative can, as already described above, ensue through central or peripheral venous injection. For example, 20 to 100 ml of a 5 to 20 weight/volume % solution of the hemoglobin derivatives can be injected into the patient in 2 to 15 mins, whereby a carbon monoxide increase in the blood of about 2.8% is created. In individual cases, the increase of carbon monoxide concentration in the blood depends on the entire hemoglobin content of the patient.

Taking of samples ensues, as described above. Even with this process it can be of advantage to take several samples, so as to ascertain via extrapolation of a regression line the concentration of carbon monoxide in the blood at the actual time of injection.

It is preferred to use blood gas analysis devices or CO-oxymetry with an optical measurement principle for determining the carbon monoxide content in blood within the context of the present invention. Here, measurements of 535, 560 and/or 577 nm are especially preferred. The volume of the sample needed for these measurements, amounts preferably to not more than 35 µl per sample. The analysis is very rapid and can be carried out in 2.5 mins.

The plasma hemoglobin concentration can be ascertained after measurement from the following equation:

$$nHb = nFCO\text{-}HB / dCO\text{-}Hb,$$

wherein nHb is the entire quantity of hemoglobin in circulation in mmol, nFCO-Hb is the administered quantity of carbon monoxide in mmol, and dCO-Hb is the increase of concentration of carbon monoxide in the blood after the carbon monoxide input (corresponding to the difference of the analysis before application of the carbon monoxide and the analysis after).

According to another embodiment of the invention the blood volume can be calculated according to the formula $$BV = nHb / cHb$$

wherein cHb is the hemoglobin concentration in mmol/l and the other abbreviations have the meaning named above.

The present invention in addition relates to a preparation for determining plasma and blood volume that contains hemoglobin derivatives which have at least in part carbon monoxide as a ligand.

For this embodiment of the invention, too, it is especially preferred that the hemoglobin derivatives should present a molecular weight of at least 128 kDa.

The preparation for diagnosis of blood volume can additionally contain acceptable carrier, auxiliary and reduction agents and the above named compounds are preferred.

The particular advantages of the use of hemoglobin derivatives according to the invention thus lie especially in the fact that the plasma and/or blood volume of a patient can be determined inexpensively and rapidly in clinical daily practice. Repeated measurements are possible. To ascertain the measured values from the samples, it is possible to use the conventional analysis devices of the prior art (spectrophotometer, densitometer, blood gas analysis device/oximetry), that make an automatic processing and analysis of the samples possible. The ascertaining of plasma and/or blood volume from the measured values can be executed by a computer, so that a fully automatic evaluation of the samples is ensured and the doctor simply has to read off the measured value of the plasma and/or blood volume.

What is claimed is:

1. A process for determining plasma and/or blood volume, comprising:
   (a) giving a defined quantity of hemoglobin derivatives to a patient,
   (b) awaiting mixture of the hemoglobin derivatives with blood of the patient,
   (c) taking at least one sample from the patient,
   (d) determining content of the hemoglobin derivatives and/or content of the hemoglobin derivatives' bound ligands in the at least one sample, and
   (e) ascertaining the plasma and/or blood volume therefrom; wherein the hemoglobin derivatives are stable chromoproteins with a molecular weight of at least 64 kDa.

2. A process according to claim 1, characterized in that the hemoglobin derivatives contain α- and/or β- globin chains or their allelic variants.

3. A process according to claim 1, characterized in that the hemoglobin derivatives have a molecular weight of at least 128 kDa.

4. A process according to claim 1, characterized in that the hemoglobin derivatives are used together with a carrier and/or auxiliary compounds.

5. A process according to claim 4, characterized in that the carrier and/or auxiliary compounds are used in a physiological solution.

6. A process according to claim 1, characterized in that the hemoglobin derivatives are used together with a reduction agent or stabilizer.

7. A process according to claim 6, characterized in that ascorbic acid, N-acetyl tryptophan or N-acetyl cysteine is used as the stabilizer.

8. A process according to claim 1, characterized in that the hemoglobin derivatives contain at least in part carbon monoxide as ligand and the carbon monoxide content in the sample of the patient is determined.

9. Preparation for determining plasma and/or blood volume containing hemoglobin derivatives, characterized in that the hemoglobin derivatives are stable chromoproteins with a molecular weight of at least 64 kDa, which carry at least in part carbon monoxide as a ligand.

10. Preparation according to claim 9, characterized in that the hemoglobin derivatives present a molecular weight of at least 128 kDa.

11. Preparation according to claim 9, characterized in that the preparation further contains pharmaceutically acceptable carriers and/or auxiliary substances.

12. Preparation according to claim 11, characterized in that the carrier and/or auxiliary compounds are used in a physiological solution.

13. Preparation according to the claim 9, characterized in that the preparation additionally contains a stabilizer.

14. Preparation according to claim 13, characterized in that ascorbic acid, N-acetyl tryptophan or N acetyl-cysteine is used as the stabilizer.

15. A process for the manufacture of a preparation according to claim 9, comprising mixing hemoglobin derivatives with a physiological solution, characterized in that the hemoglobin derivatives are stable chromoproteins with a molecular weight of at least 64 kDa, which at least in part carry carbon monoxide as a ligand.

16. A process according to claim 15, further comprising adding auxiliary or carrier compounds.

17. A process according to claim 16, wherein Ringer's lactate, sodium chloride, sodium phosphate, solutions containing polysorbate and/or EDTA are used as auxiliary or carrier compounds.

18. A process according to claim 15, further comprising introducing stabilizers.

19. A process according to claim 18, whereby ascorbic acid, N-acetyl tryptophan or N acetyl cysteine are used as the stabilizer.

20. A process according to claim 5, characterized in that Ringer's lactate, sodium chloride, sodium phosphate, polysorbate and/or EDTA are used in the physiological solution.

21. Preparation according to claim 12, characterized in that Ringer's lactate, sodium chloride, sodium phosphate, polysorbate and/or EDTA are used in the physiological solution.

22. A process according to claim 1, characterized in that the hemoglobin derivatives contain $\alpha$- and/or $\beta$- globin chains which are linked intra-molecularly.

23. Preparation according to claim 9, characterized in that the hemoglobin derivatives contain $\alpha$- and/or $\beta$- globin chains which are linked intra-molecularly.

24. A process according to claim 15, characterized in that the hemoglobin derivatives contain $\alpha$- and/or $\beta$- globin chains which are linked intra-molecularly.

* * * * *